(12) United States Patent
Linde et al.

(10) Patent No.: US 6,479,056 B1
(45) Date of Patent: Nov. 12, 2002

(54) LIVE VACCINE CONSTITUTING MINOR RISK FOR HUMANS

(75) Inventors: Klaus Linde, Leipzig (DE); Jörg Beer, Hänselweg (DE); Bärbel Pless, Leipzig (DE)

(73) Assignee: Lohman Animal Health GmbH & Co. KG, Cuxhaven (DE)

( * ) Notice: Subject to any disclaimer, the term of this patent is extended or adjusted under 35 U.S.C. 154(b) by 0 days.

(21) Appl. No.: 09/686,113

(22) Filed: Oct. 11, 2000

Related U.S. Application Data

(60) Division of application No. 08/802,127, filed on Feb. 19, 1997, now Pat. No. 6,136,325, which is a continuation-in-part of application No. 08/300,600, filed on Sep. 2, 1994, now abandoned.

(51) Int. Cl.[7] ..................... A61K 39/112; A61K 39/02; A61K 39/00; A01N 63/00

(52) U.S. Cl. ................. 424/258.1; 424/234.1; 424/184.1; 424/93.48; 424/816; 424/200.1

(58) Field of Search ........................... 424/258.1, 236.1, 424/184.1, 816, 93.1, 93.4, 93.48, 200.1

(56) References Cited

PUBLICATIONS

Silva et al. Pesqui Vet. Bras. 4 (4): 143–145, 1984, abstract.*

* cited by examiner

*Primary Examiner*—S. Devi
(74) *Attorney, Agent, or Firm*—Vidas, Arrett&Steinkraus PA

(57) ABSTRACT

A salmonella live vaccine produced from at least one attenuated immunologic live vaccine strain, characterized in that the vaccine strain has an envelope marker which results in an increased sensitivity of the vaccine strain toward a specific therapeutically effective antibiotic and has at least one chromosomal antibiotic resistance mutation for the attenuation.

1 Claim, 1 Drawing Sheet

LIVE VACCINE CONSTITUTING MINOR RISK FOR HUMANS

CROSS-REFERENCE TO RELATED APPLICATIONS

This application is a Divisional of application Ser. No. 08/802,127 filed Feb. 19, 1997, now U.S. Pat. No. 6,136,325, which is a continuation-in-part of application Ser. No. 08/300,600, filed Sep. 2, 1994, now abandoned. The contents of the above patent and applications are herein incorporated by reference in their entirety.

BACKGROUND OF THE INVENTION

1. Field of the Invention

This invention relates to a special use of a live vaccine, to new live vaccines not having been used before, to a method of producing such vaccines as well as to suitable vaccine strains, especially salmonella.

2. Description of the Related Art

The majority of salmonella-conditioned Gastroenteritis infectiosa of humans are caused by contaminated animal products. Especially chicken and chicken eggs, respectively, being infected with the at present predominantly occurring serovar Salmonella enteritidis have increasingly been causing infections, recently. Nevertheless, generally all food stuffs are affected which originate from animals kept in mass-rearing. Here, normally many animals are kept in confined space, promoting the spread of infections among the animal stock.

The risk of a transmission of the infection from the infected animal to humans can be reduced by customary veterinary medical measures for the interruption of infection chains. Furthermore, thorough compliance with I kitchen hygiene regulations during the processing of contaminated animal products can prevent a transmission to humans. However, especially the latter regulations are not always being considered during the storage and processing of food. Therefore, it is imperative to rule out the possibility of infected animals being processed right from the beginning. This can be achieved e.g. through a vaccination of the animal stock against salmonella infections.

Suitable salmonella live vaccines have to comply with various different conditions:
1. The virulence of the vaccine strains used in the production of the vaccines has to be adjusted in a way that guarantees a non-apparent infection on the one hand, and a sufficient persistence of the vaccine strains in the host tissue on the other hand, as a prerequisite for high immunogenicity.
2. Furthermore, the stability of the vaccine strains used with respect to their virulence and their protective properties has to be widely assured, I.e. it has to be assured that they do not mutate back into the virulent wild strain.
3. To allow for the reduction of the probability of infections it should be ascertained that the vaccine strains are not permanently being excreted alive and that they can only service for a short period of time in the environment, respectively.

The above-mentioned three conditions, which a live vaccine has to comply with, are to be discussed in detail in the following. As described in 1, the production of a suitable salmonella live vaccine is based on a reduction of the virulence (attenuation) of the pathogenic salmonella and simultaneous preservation of their antigen structures, and thus, the immunogenic effect in the host. One possibility is e.g., to employ deletion mutants, e. g. pur or aro auxotrophic clones, as vaccine strains. The attenuation level of these vaccine strains depends upon the lack of metabolites in vivo, which possibly impedes an accurate adaptation to the host to be immunized. In this respect, it is referred to the EP 0 263 528 in which stable asp mutants of Salmonella typhimurium with different virulence reduction levels are described. Vaccine strains with attenuation levels adapted to each of the different host species can be produced by selecting suitable asp mutants.

A further possibility for an attenuation consists of the employment of vaccine strains, the virulence reduction of which can be traced back to a metabolism drift mutation (called stwd mutation or marker in the following). The term "metabolism drift" comprises all essential enzymes and functionally important cell compartments, respectively, having been functionally altered by mutations, as e.g. ribosome proteins, gyrase, RNA polymerase, permease, wherein, as a result of these mutations, translation, DNA replication, DNA transcription or permeation are more or less distinctly disturbed. Such stwd mutants, furthermore, show a resistance with respect to specific antibiotics and other substances (noxious substances). Stwd mutants can easily be obtained in laboratories as chromosomal antibiotic resistance mutants. In this respect, from the EP 0 263 528 e.g. stwd mutants with a resistance against nalidixic acid (Nal), streptomycin (Sm) or rifampicin (Rif) are known. Especially if several stwd markers are incorporated into one vaccine strain (double or triple marker vaccine strain), de facto unlimited possibilities are obtained for the production of a desired attenuation level adapted to suit every specific host species.

With respect to the prior art "attenuation by means of stwd mutations" it is referred to the following publications: DD-WP 155 294; DD-WP 218 834; DD-WP 235 828; DD-WP 253 182; DD-NP 253 184; DD-WP 281 118; DD-WP 294 420; EP 0 263 528.

A further (mentioned above under 2) condition is that the attenuated vaccine strains obtained by mutation do not mutate back into the virulent wild strain. The required stability can, on the one hand, be achieved by only employing vaccine strains with which no reversions can be detected in vitro or whose reversion ratios are $<10^7$. A further possibility is to employ vaccine strains comprising several mutations which independently reduce virulence. Here, the probability of a back mutation can almost be excluded.

The final condition, mentioned above under 3 in connection with the term "interruption of infection chains", especially concerns the risks with respect to a possible excretion and permanent survival of the vaccine strains outside the vaccinated host. In this respect, it is desirable to reduce the excretion and the capability of survival of the vaccine strains in the environment. To guarantee a sufficient immune response, on the other hand, the capability of temporary survival of the vaccine strains in the host tissue after e. g. oral or parenteral application should only be slightly impaired or not at all. Vaccine strain mutants complying with such requirements are known e.g. from the DD-WP 218 836, DD-WP 231 491, DDWP 253 182, DD-WP 253 183, DD-WP 253 184, and EP 0 263 528. In the prior art it is suggested to optimize suitable vaccine strains by employing so-called anti-epidemic markers for the reduction of excretion and the capability of survival in the environment. The term anti-epidemic marker characterizes outer envelope mutations in a broader sense, causing a functional variation of the permeability barrier in the outer membrane.

Vaccine strains can be provided with different anti-epidemic markers depending upon the intended application form. The anti-epidemic markers known at present are divided into three groups, depending on the alterations they cause in the outer membrane of the vaccine strain. The first group comprises the so-called hst markers. The incorporation of an hst marker causes the vaccine strain to become highly sensitive towards bile, anionic detergents, macrolide antibiotics and other noxious substances. Owing to the high sensitivity towards bile, there is a reduced excretion with feces caused by the inactivation of the vaccine strains already occurring in the intestinal lumen. If vaccine strain bacteria are excreted, they only have a shortened survival time in the environment, due to the lack of the permeability barrier in the outer membrane against tensides and macrolides and other noxious substances. Therefore, an infection can almost be excluded when using vaccine strains including hst markers. When employing the usual doses of vaccine, vaccine strains comprising hst markers can only be applied parenterally, however. If applied orally, due to the high sensitivity towards bile, the virulence is influenced to such an extent that a sufficient immune response can only be achieved by employing extremely high doses of vaccine. Therefore, the solution for an oral application would be to provide vaccine strains including an anti-epidemic marker from one of the other two known groups. One group comprises the so-called rbt markers (reversion to bile tolerance). The rbt marker can be obtained by mutation from the hst marker. It provides the vaccine strain with an anti-epidemic potency just as the hst marker does. However, in contrast to the hst marker the vaccine strain comprising an rbt marker is tolerant towards bile, and can therefore be applied orally without a reduction of the virulence impairing the vaccination effect. The same stands for a further group, the so-called rtt marker (reversion to tenside tolerance). The rtt marker can be obtained by mutation from the. rbt marker. The vaccine strain comprising the rtt marker is tolerant towards tensides and simultaneously possesses a sufficient anti-epidemic potency due to the remaining high sensitivity towards macrolides and other noxious substances. Also the rtt marker strain can be applied orally without any problems.

Taking this information and these publications as a basis, live vaccines can be produced which comply with all conditions required. The adaptation to the respective host can be effected, e.g. in animal test series.

A further problem remains to be solved. Even the compliance with all precautions does not exclude the possibility of a person dealing e.g. with the vaccination of the animals or the production of the vaccines, coming into contact with the in fact attenuated but, nevertheless, still pathogenic salmonella vaccine strains. Where healthy people are concerned, there is hardly any risk of an infection. However, if the immune system of people is weakened (e.g. by an HIV-infection), the contact with such vaccine strains can result in a salmonella infection.

Therefore, the object of the invention is to provide a live vaccine against salmonella infections, starting from the known prior art, being optimally attenuated for the host to be immunized, providing it with an immunity for reducing the excretion of wild strains when applied orally or parenterally, and constituting only a minor risk for people, especially those with a weakened immune system, or none at all. A further object of the invention is to provide a method for producing salmonella live vaccines optimally suited to the respective host by employing significantly less animal experiments than the conventional methods. Finally, the invention is to provide salmonella live vaccine strains for live vaccines suitable for chickens and poultry in general.

This object is attained by a specific live vaccine, a specific method for the production of salmonella live vaccines, and live vaccine strains.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

The invention concerns the use of a live vaccine strain known as such (see e.g., EP 0 263 528) for the production of a specific live vaccine. The known salmonella live vaccine strains comprise an envelope marker as well as an attenuation marker (e.g. auxotrophy marker or stwd marker) providing them with an anti-epidemic potency (reduced excretion by the host and reduced survival rate in the environment, respectively). The envelope marker being employed there, furthermore, causes a sensitization of the vaccine strains towards macrolide antibiotics. This antibiotic sensitization has, hitherto, merely been employed for the selection of suitable envelope mutants, i.e. in the production of vaccine strains. According to the invention it has been recognized for the first time that the macrolide sensitivity of the vaccine strains comprising an envelope marker can also function as a safety mechanism when employing the vaccine strains produced in this manner. The vaccine is to be designed such that, in the case of it causing an infection of another host, an effective therapeutical treatment of the infected host can be carried out by means of macrolides. This aim is achieved relatively easily by selecting only such vaccine strains (provided with an envelope marker) for the production of the vaccine whose propagation can be controlled by the application of justifiable doses of macrolide antibiotics.

The known salmonella live vaccine strains used in a specific manner show a sensitivity towards macrolides, due to their envelope marker. In addition to envelope mutants having an increased sensitivity towards hydrophobic antibiotics (macrolides, e. g. erythromycin) also other envelope mutants are described (I. A. Hancock, R. E. W.: *Ann. Rev. Microbial.* 1984, 38, 237–264), occasionally having different permeabilities with respect to a sensitivity towards hydrophilic, hydrophobic and polycationic antibiotics. Such envelope markers have been insignificant in the production of bacterial live vaccines, hitherto.

The invention also concerns live vaccines which are produced by including at least one attenuated live vaccine strain having an envelope marker providing the vaccine strain with an increased sensitivity towards a specific therapeutically effective antibiotic with the exception of macrolides. The live vaccine strains being employed in the production of the salmonella live vaccine according to the invention, therefore, comprise an envelope marker generally providing them with an anti-epidemic potency (interruption of infection chains) and, optionally, a sensitivity towards macrolides, but, in any case, an increased sensitivity towards another specific therapeutically effective antibiotic. The vaccine strains can be detected relatively easily by employing the selected specific therapeutically effective antibiotic, so that the production of a vaccine strain provided with a suitable envelope marker does not create a great problem. It is understood that with respect to an optionally required possibility of treatment for an unwanted infection caused by the vaccine, preferably such antibiotics are selected which constitute good results with respect to the salmonella serovars employed.

Furthermore, it is understood that the selected live vaccine strains are derived from predominant serovars, those of salmonella chosen for practical application including *Salmonella typhimurium* and *Salmonella enteritidis*, accession numbers DSM 9361 and DSM 8432.

As mentioned above, there are various possibilities for the attenuation of live vaccines. One possibility is to include an auxotrophy marker (e.g. asp~) into the vaccine strain. Preferably, the vaccine strain is provided with at least one chromosomal antibiotic resistance mutation. The term chromosomal antibiotic resistance substantially comprises the above-mentioned stwd markers. It has been proven that by employing selected stwd markers and by a specific combination of several such markers, respectively, the attenuation level of the vaccine strain can be adapted optimally. Upon the selection of such chromosomal antibiotic resistance mutations for the attenuation of vaccine strains, it has to be secured that they do not exclude the increased sensitivity caused by the envelope marker towards the therapeutically effective antibiotic. Therefore, during development of the vaccine strain it is sensible to firstly determine which therapeutically effective antibiotic is to be employed for the possibility of treatment of the vaccine strain. Dependent upon this, the vaccine strain and its chromosomal antibiotic resistance mutation, respectively, are selected for the attenuation of the vaccine strain.

According to a further preferred embodiment of the invention, the envelope marker is selected such that it provides the vaccine strain (besides an anti-epidemic potency and an optional macrolide sensitivity) with an increased sensitivity towards an antibiotic of the group including quinolons, chloramphenicols or tetracyclines. Especially preferred is an envelope marker providing the vaccine strain with an increased sensitivity towards the antibiotic ciprofloxacin, presently the most effective antibiotic against salmonella. During the production of the latter vaccine strain, it is especially advantageous to provide a metabolism drift mutation, resulting in a streptomycin and/or rifampicin resistance, for the attenuation. These antibiotic resistances do not interfere with a possible sensitivity of the vaccine strain towards the antibiotic ciprofloxacin.

Depending on the desired effective spectrum, the salmonella live vaccine according to the invention can be produced from one or several vaccine strains of different serovars of the O-groups B (e.g. *Salmonella typhimurium*), D (e. g., *Salmonella enteritidis*), C (e.g., *Salmonella infantis*) and E (e.g., *Salmonella anatum*) as mono, bi, tri or tetra-vaccine.

A further problem, already mentioned above, is constituted in that, due to different sensitivities, a specifically adapted live vaccine has to be provided for every host. In this respect, it is referred to the already traded *Salmonella typhimurium* vaccine "Zoosaloral Dessau" which sufficiently immunizes calves after a single oral application, however, does not protect chickens against an I. p. toxic infection until three times oral vaccination (Linde, K. et al.: *Vaccine* 1990, 8, 278–282). Zoosaloral is a vaccine from Impfstoffwerk Dessau-Tornau GmbH and has two auxotrophy markers $Pur^-$ $his^-$. The double marker attenuation is based upon the purine dependence (deficiency of purine available in the host) and an accidental co-mutation in the rfb locus adjacent to the histidin operon for the S-type polysaccharide synthesis, which co-mutation results in the leaky function. Zoosaloral is overattenuated for chicks. With respect to the sensitivity towards *Salmonella typhimruium,* dependent upon the host species, a hierarchy mice>calves>chickens can be constituted. From this it follows that e.g., *Salmonella typhimruium* vaccine strains for chicks and chickens have to have a lesser attenuation level (in comparison with mice) for the compensation of the lesser sensitivity. It can be assumed that the same correspondingly stands for other salmonella serovars.

It has been found that the generation times of salmonella live vaccines generally correlate with their attenuation levels. This correlation between generation time and attenuation level especially occurs if the vaccine strains have been provided with a chromosomal resistance mutation for the attenuation.

The relation between generation time and attenuation level permits a relatively reliable selection of vaccine strains being suitable for a specific host without prior animal experiments. In this respect, a suitable live vaccine for the immunization of chicks and chickens produced of at least one attenuated vaccine strain has a generation time thereof being about 28 to 34 minutes. Vaccine strains with such generation times have a lower attenuation level (in comparison with the vaccine strains of calves and mice), compensating the small sensitivity of chicks/chickens towards e.g., *Salmonella typhimurium* (S. tm) and other salmonella serovars.

As mentioned above, an effective salmonella vaccine is especially interesting with respect to the host species chicks/chickens. However, it has also been applied with ducks and ducklings and should be useful for poultry in general since they all have the relatively short lives problem that allows for the possibility of live virus in their meat. The *Salmonella typhimruium* stwd mutants, having been deposited/published hitherto, have no direct relation to this host species. Vaccines are introduced which can be optimally attenuated for chicks/chickens, or have already been optimally attenuated. In this respect, the vaccine strain S. tm Nal 2/Rif 9/Rtt is emphasized which is optimally attenuated for chicks/chickens. The same stands for the vaccine strain S. tm Nal 2/Rif 9 which has not been deposited, yet, with respect to this application, but still is to be commented on. The vaccine strains cited have a generation time of about 32 minutes. From this fact the "attenuation equivalent generation time" for the selection of optimally attenuated other strains of the same or other serovars has been derived. Nevertheless, with respect to the selection of suitable vaccine strains for chicks/ chickens generation times vary from 28 to 34 minutes. This diversity acknowledges the fact that chicks/chickens have different sensitivities towards different strains and strain-dependent differences in virulence is of each serovar, respectively. By means of a few test series, from the preselected vaccine strains having generation times between 28 and 34 minutes those can be chosen which are optimally attenuated for chicks/chickens. Advantageously, this at least allows for the animal experiments required in the preselection to be dropped.

Furthermore, with respect to the possible host chicks/chicken it is especially interesting if, as proposed according to the invention, a salmonella live vaccine is used comprising a vaccine strain with an increased sensitivity towards a specific therapeutically effective antibiotic. Chickens have a relatively short life span in comparison with other host species, as e.g., humans, calves or piglets. In general, they are slaughtered after a comparatively short rearing period and sold as frozen or fresh meat. Since the vaccination has not taken place very far in the past, it can be assumed that there are still live salmonella vaccine strain bacteria within the chickens at the time of slaughter. These can then find their way into the environment. For the normal population the small amounts of germs in question are insignificant. The risk of an infection can almost be excluded in this respect. Nevertheless, in individual cases risk patients with weakened immune systems (e.g., people with the HIV-virus) can be infected and react with clinical symptoms. Especially with respect to these people, it is required that an infection caused by the vaccine strain may be controlled rapidly and without any problems. With respect to this, the incorporation of a sensitivity towards therapeutically effective antibiotics as a safety and therapy marker is a sensible alternative, excluding all theoretical reservations.

The prototype of such a safety and therapy marker is the so-called ssq marker. Vaccine strains having an ssq marker possess a hypersensitivity towards quinolons, especially towards ciprofloxacin, at present, being the most effective antibiotic against salmonella. Also the ssq marker, like the above-mentioned hst, rbt and rtt mutations, is an envelope mutant and, therefore, also has a more or less distinctive anti-epidemic potency dependent upon its bile and anionic detergent tolerance and sensitivity, respectively.

The invention not only deals with the production of especially safe live vaccines. A further object is to provide a method for the production of a live vaccine optimally attenuated for a specific host employing hardly any animal experiments.

The principle of this method is based on the fact that an attenuation of vaccine strains (especially with respect to the incorporation of stwd markers) leads to a prolongation of the generation times in comparison with the wild strain. It has already been mentioned above that the prolonged generation times may allow for a conclusion with respect to the attenuation level of the vaccine strains. In conformity with the method according to the invention, it is therefore sufficient to determine the specific prolonged generation time of a vaccine strain suitable for a host in a single test (e.g., an animal experiment). The prolonged generation time determined such can then serve as an approximate figure for the following selection of further vaccine strains (of the same serotype), or it can be transferred to other serotypes of the same genus as an attenuation equivalent.

For the production of a vaccine optimally suited to chicks/chickens, e.g., a vaccine strain is selected, the generation time thereof being prolonged to about 28 to 34 minutes in comparison with the wild strain (22 minutes). The vaccine strain employed may e.g., be attained from a wild strain having been provided with a streptomycin (Sm) or nalidixic acid (Nal) marker. Through this, a prolongation of the generation time from 22 minutes to 25 to 29 minutes is achieved. Subsequently, a rifampicin (Rif) marker is incorporated as a further marker prolonging the generation time.

According to the essential features of the method a vaccine can be produced:

in a first step, by isolating stwd mutants of a phenotype having a specific antibiotic resistance and showing a generation time being prolonged by about 3 to 6 minutes in comparison with salmonella wild strains, for the purpose of producing strains with small or moderate attenuation, in a second step, by again isolating stwd mutants of another phenotype with an antibiotic resistance from these lesser or moderately attenuated single marker strains, again having a generation time being prolonged by an additional 3 to 6 minutes, whereby a set of vaccine strain candidates is being achieved having prolonged generation times graded from about 28 to 34 minutes (wild strain about 22 minutes)—which with respect to S. tm in the mouse model (since the logarithm of an $LD_{50}$ correlates linearly with the (prolonged) generation time) corresponds to graded $LD_{50}$ values of about $10^5$ to $10^7$ (wild strain about $10^1$) cfu—then once orally immunizing ≧36 hours old chicks with $10^9$ cfu of the individual vaccine strains of this set, after two weeks orally infecting the immunized animals with $10^6$ cfu of the wild strain, and finally favoring the S. tm Nal 2/Rif 9 strain with a (prolonged) generation time of about 32 minutes (and an i.p. $LD_{50}$ mouse of about $10^6$ cfu) as the favorite prototype vaccine strain with respect to the relation of "maximum possible prolongation of generation time/attenuation level and yet optimal reduction of the excretion of wild strain", for the determination of the "attenuation equivalent (prolonged) generation time" for other strains of the same serovar and serovars with only moderate or lacking virulence towards mice, respectively.

in a third step, by incorporating an "ssq safety and therapy" marker into the double marker vaccine strains attenuated by means of stwd mutation, for the optimization of the vaccine strains/increase of the acceptance, the safety and therapy marker approximately quadrupling the sensitivity towards ciprofloxacin (chloramphenicol, doxycycline, etc.) and simultaneously insignificantly reducing the excretion and capability of survival in the environment.

The sequence described is arbitrary, and noxious substance resistance phenotypes (DD-WP 235 828) may also be used.

Furthermore, the invention relates to specific salmonella vaccine strains, having generation times of 28 to 32 minutes, as well as to variants on these vaccine strains having higher or lower attenuation levels and generation times between 28 and 34 minutes. Finally, the use of such vaccine strains for the oral immunization of chicks as well as the oral and parenteral immunization of chickens against salmonella infections is described.

The vaccine strains (with or without ssq markers) referred to in the claims and the following examples (as well as having been deposited) are examples for all the vaccine strain candidates with graded attenuation levels which may be produced. They are suitable for the production of immunogenic live vaccines, especially for chicks/chickens according to propagation methods known as such. With respect to the specifically stated vaccine strains having ssq markers, (and deposit members DSM 8433, 8435, 9362, 8434, 8441, 8432), generation times of about 32 minutes are indicated. Further specific strains having ssq markers have generation times of about 28 minutes (deposit number 9361) and about 30 minutes (deposit number 9360). This statement with respect to generation time is not to be understood as a restriction. Taking strain-dependent differences in virulence (invasive capacity/colonization activity) into account, generation times of 28 to 34 minutes are also possible as attenuation equivalents. All deposit numbers referred to herein are with Deutsche Sammlung von Mikroorganismen und Zellkulturen GmbH, a Budapest Treaty Depository.

The live vaccine based on *Salmonella typhimruium* Nal 2/Rif9/Rtt DSM 8432 has bene found to impede intestinal colonization by other bacteria or pathogens and thereby also protects the host against other infections. This effect is also predicted with the other strains of the invention.

In the following table the salmonella vaccine strains favored for the different serovars are listed.

| Salmonella serovar | Vaccine strains clone | Laboratory number | Deposit number*) |
|---|---|---|---|
| typhimurium | Ssq/Sm 60/Rif 42 | 4242 | DSM 8433 |
| enteriditis | Ssq/Sm 24/Rif 12 | 4266 | DSM 8435 |
| | Ssq/Sm 24/Rif 12k | 4298 | DSM 9362 |
| | Ssq/Sm 24/Rif 12g | 4297 | DSM 9361 |
| | Ssq/Sm 24/Rif 3 | 4296 | DSM 9360 |
| infantis | Ssq/Sm 153/Rif 7 | 4289 | DSM 8434 |
| anatum | Ssq/Sm 81/Rif 21 | 4279 | DSM 8441 |
| typhimurium | Nal 2/Rif 9/Rtt | 4223 | DSM 8432 |

*)the microorganisms were deposited at: DSM - Deutsche Sammlung von Mikroorganismen und Zellkulturen GmbH, Mascheroder Weg 1 B, D-38124 Braunschweig, Germany In the following the invention is to be described in detail by several examples of embodiments.

BRIEF DESCRIPTION OF THE DRAWINGS

A detailed description of the invention is hereafter described with specific reference being made to the drawings in which.

DESCRIPTION OF THE PREFERRED EMBODIMENTS

Figure 1:
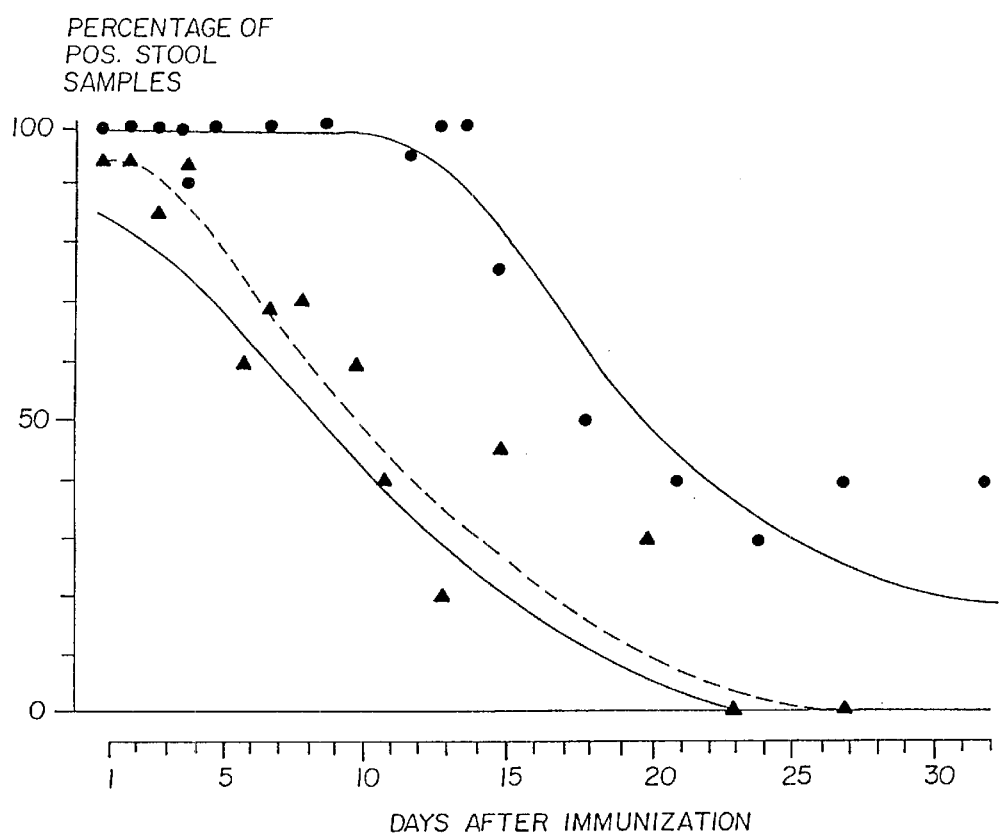
FIG. 1 is a Graph showing Frequency (% positive samples) and Duration (last positive result).

Material and Method
Strains Used
  wild strains
    S. typhimurium (S. tm) 415 (Metschnikov-Institute, Moscow), i.p. $LD_{50}$ mouse $\geq 10^1$ cfu, generation time≈22 min.
    S. enteritidis (S. ent) 318 (Prof. Selbitz, University of Leipzig), i.p. $LD_{50}$ mouse—$10^5$ cfu, generation time—22 min.
    S. infantis (S. inf) (Dr. Beer, Veterinärunter-suchungsamt Chemnitz), generation time—22 min.
    S. anatum (S. ana) (Dr. Beer, Veterinärunter-suchungamt Chemnitz) generation time~22 min.
  wild strains having a neutral nalidixic acid and streptomycin resistance for the detection of the reduced excretion upon immunized chicks/chickens.
    S. tm Nal/Sm, generation time≈22.5 minutes
    S. ent Nal/Sm, generation time≈22.5 minutes
    S. inf Nal/Sm, generation time≈22.5 minutes
    S. ana Nal/Sm, generation time≈22.5 minutes
  wild strains as examples for other double or triple marker mutants with lower (or higher) attenuation/ correspondingly less or more prolonged generation time:
    S. tm Ssq/Sm 60/Rif 42, generation time≈31 min., laboratory no. 4242; deposit no. DSM 8433
    S. ent Ssq/Sm 24/Rif 12, generation time≈32 min. laboratory no. 4266; deposit no. DSM 8435
    S. ent Ssq/Sm 24/Rif 12k, generation time≈32 min. laboratory no. 4298; deposit no. DSM 9362
    S. ent Ssq/Sm 24/Rif 12g, generation time≈28 min. laboratory no. 4297; deposit no. DSM 9361
    S. ent Ssq/Sm 24/Rif 3, generation time≈30 min. laboratory no. 4296; deposit no. DSM 9360
    S. inf Ssq/Sm 153/Rif 7, generation time≈31 min. laboratory no. 4289; deposit no. DSM 8434
    S. ana Ssq/Sm 81/Rif 21, generation time≈32 min. laboratory no. 4279; deposit no. DSM 8441
    S. tm Nal 2/Rif 9/Rtt, generation time≈32 min. laboratory no. 4223; deposit no. DSM 8432 as a prototype strain (with optimal attenuation for chicks/ chickens) for the determination of the "attenuation equivalent (prolonged) generation time".

Nutrient Media
  Nutrient agar (SIFIN, Berlin-Weißensee)
  Tryptose phosphate broth (Difco, U.S.A.)

| Antibiotics | |
|---|---|
| nalidixic acid | (CHINOIN, Budapest) wild strains MHK 6.2 ug/ml |
| streptomycin | (Jenapharm) wild strains MHK 6.2 ug/ml |
| rifampicin | (UBM, Bucarest) wild strains MHK 12.5 ug/ml |
| ciprofloxacin | (Bayer) wild strains MHK 0.05 ug/ml |
| chloramphenicol | (Berlin-Chemie) 2.0 ug/ml |
| doxycycline | (Jenapharm) wild strains MHK 4.0 ug/ml |
| erythromycin | (Abbott) wild strains MHK 60.0 ug/ml |

Test Animals and Conditions of Keeping
  Chicks of hens laying brown eggs from different breeding stations were kept in cages by 5–10 animals and fed with turkey feed as well as water ad libitum.

Oral Immunization
  Groups of 10 chicks each had a single dose of $10^9$ cfu, partly $10^8$ cfu, of the respective vaccine strain applied orally into their gullets, either 36 hours after hatching or (for the purpose of comparison and determination of the optimal immunization age) on the fourth day of their lives. The immunization under practical conditions is also possible via the drinking water (after water deprivation for 4 hours an amount of drinking water of 2 ml/chick is taken in within 3 hours).

Oral Infection
  Two to four weeks after the oral immunization the chicks orally received $10^6$ cfu (or $10^7$ cfu) of the respective neutrally marked homologous wild strain by means of a pipette.

Detection of the Excretion
  vaccine strain S. tm Ssq/Sm 60/Rif 42, S. ent Ssq/Sm 24/Rif 12, S. inf Ssq/Sm 153/Rif 7 and S. ana SsqJSm 81/Rif 21: nutrient media containing 100 ug rifampicin and 200 ug streptomycin/ml;
  vaccine strain S. tm Nal 2/Rif 9 with or without rtt marker: nutrient media containing 100 ug rifampicin and 12.5, ug nalidixic acid/ml;
  neutral Nal/Sm marked wild strains: nutrient media containing 100 ug nalidixic acid and 200 ug streptomycin.
  Per chick group and day of examination, five fresh stool samples each were suspended in 2 ml physiological sodium chloride solution and, additionally, dilutions from $10^{-1}$ to $10^{-4}$ were produced.
    quantitative determination: 0.1 ml of the original suspension and the dilutions, were applied onto nutrient agar with each 1% lactose and saccharose, 0.015% bromthymol blue (determination of the number of coli/ enterobacteria germs) by means of a spatula. Parallel to this, both were applied onto the same medium containing the respective antibiotic. As a quantitative measure for the excretion and the reduction of salmonella colonization occurring in immunized chicks in comparison with the controls, the number of salmonella colonies vs. the number of enterobacteria colonies was determined in thousandths.
    qualitative determination: an antibiotic bouillon was added to the remaining original suspension. After incubation for 24 hours at 37° C., the salmonella were transferred onto nutrient agar containing the respective antibiotic additives.

The confirmation of the grown salmonella was effected serologically, biochemically, and through the determination of the markers.

As a quantitative measure for the excretion and the reduction of salmonella colonization occurring in immunized chicks in comparison with the controls, the number of salmonella colonies vs. the number of enterobacteria colonies was determined in thousandths.

EXAMPLE 1

S. tm: Isolation of spontaneous chromosomal antibiotic resistance clones as (Nal-twd single and) Nal/Ri-stwd double marker strains having graded prolonged generation times between about 29 to 34 (wild strain about 22) minutes for the isolation of a prototype vaccine strain for the determination of the "attenuation equivalent (prolonged) generation time" for strains of the same serovar and serovars having only moderate (S. ent) or lacking (S. inf and S. ana) virulence towards mice, respectively. $10^9$ (and $10^{10}$) cfu of the wild strain are transferred onto nutrient agar containing 100 ug (or in two steps of 50 ug and afterwards 400 ug) nalidixic acid/ml by means of a spatula and incubated for approximately two days at 37° C. The resistance clones are transferred onto nutrient agar, controlled with respect to obtained resistance, and the less or more reduced extinction is determined (Spekol with tube samples, Zeiss-Jena, wave length 650 no, starting germ count $10^7$ cfu, incubation in shaking water bath for 3 hours at 37° C.). The generation times of clones appearing to be suitable are measured by means of the Abbott MS-2 test system. As described above, on nutrient agar with 400 ug rifampicin/ml, resistance clones are attained from clone Nal 2 having a generation time of about 28 minutes. The generation times of these resistance clones are determined, and the Nal 2/Rif clones having graded prolonged generation times between about 29 and 34 minutes are used for the determination of the approximate figure (prolonged) "generation time as an attenuation equivalent" (see example 3).

EXAMPLE 2

Detection of obtained colonization activity of the neutrally Nal/Sm marked S. tm, S. ent, S. inf and S. ana wild strains in 17 to 25 days old chicks.

17 to 25 days old chicks orally received $10^6$ (or $10^7$) cfu of neutrally marked wild strains by means of a pipette. During a period of 10 to 15 days the quantitative salmonella colonization density was determined in comparison with the number of enterobacteria germs.

In the selected infection model (dose $10^6$ to $10^7$ cfu), after oral infection, either the excretion of the neutrally marked wild strains with high germ counts already occurs after 24 hours, or the salmonella germ counts gradually only reach their highest figures in the stool between the third and the sixth day (maximum figures at a 50 thousandth of the total enterobacteria flora). After eight to ten days, the number of salmonella colonies drops to a 1.0 to 0.1 thousandth of the enterobacteria flora, and remains in this range for a longer period of time.

This colonization dynamism demonstrates that the neutrally Nal/Sm marked wild strains are suitable for the determination of a reduced wild strain colonization in immunized chicks.

EXAMPLE 3

Determination of the S. tm Nal 2/Rif prototype vaccine strain having a (prolonged) generation time/attenuation level optimally suited to chicks/chickens by means of the relation of maximum possible prolonged generation time/attenuation level and yet optimal reduction of excretion of wild strain, for the purpose of the determination of the "attenuation equivalent (prolonged) generation time" for strains of the same serovar and of serovars having only moderate or lacking virulence towards mice, respectively.

Chicks at the age of $\leq 36$ hours were immunized orally with $10^9$ cfu of the different strains from the set of S. tm double marker strains having graded generation times between 29 and 34 minutes and, after two weeks, were infected orally with $10^6$ cfu of the wild strain. Parallel to this, control chicks of the same age were infected orally.

In comparison with the controls, the immunized chicks which received the vaccine strains having graded generation times between 29 and 34 minutes, show a significantly reduced excretion of the wild strain (determined from the enterobacteria colonization density in thousandth), especially in the first five to ten days after the oral challenge. The variation (reducing with time) lies within the range of one to two tenth powers. From the sixth to the tenth day after the oral challenge the salmonella colonization densities in immunized chicks come into closer alignment with those of the controls (in the 0.1 thousandth range of enterobacteria germ counts). In individual cases, however, immunized chicks may show a reduced excretion in the range of one log step, even after the tenth day.

With respect to vaccine strains having generation times of ≧33 minutes the excretion of wild strain is reduced significantly less, wherein the difference to the controls generally does not exceed a tenth power. On the basis of the relation: "maximum possible prolonged generation time/attenuation level and yet optimal reduction of excretion of wild strain", the S. tm Nal 2/Rif 9 having a generation time of about 32 minutes (and an i.p. $LD_{50}$ mouse of about $10^6$ cfu) was determined as a prototype vaccine strain, and its (prolonged) generation time of about 32 minutes was used as the approximate figure "attenuation equivalent".

EXAMPLE 4

Recognition/detection of the *Salmonella typhimruium* clone S. tm Nal 2/Rif 9 (I. p. $LD_{50}$ mouse about $10^6$ (wild strain about $10^1$ ) cfu; generation time prolonged from 22 to 32 minutes as an attenuation equivalent), optimally attenuated for chicks/chickens, as the favorable vaccine strain over the equivalent protective effect against a toxic infection conveyed by means of an i.p. and oral immunization; (with respect to a corresponding transfer of these regularities to further "enteritidis" salmonella):

a. Preliminary test of the extremely differentiated sensitivity of chicks/chickens and mice towards *Salmonella typhimruium* by determining the i.p. $LD_{50}$ rate of the S. tm wild strain and the S. tm Nal 2/Rif 9 vaccine strain for chicks and mice.

For mice and two-day chicks the different i.p. $LD_{50}$ rates of the S. tm wild strain and the S. tm Nal 2/Rif 9 vaccine strain as well as, additionally, the i.p. $LD_{50}$ rate of the wild strain for 17 days old chicks, are depicted in table 1.

TABLE 1

S. tm wild strain and S. tm Nal 2/Rif 9 vaccine strain: comparative i.p. $LD_{50}$ rates of mice and chicks

| S. tm | 2-day chicken (cfu) | 17-day chicken (cfu) | ICR mice (cfu) |
|---|---|---|---|
| wild strain | $10^6$ | $10^8$ | $10^1$ |
| Nal 2/Rif 9 | $10^7$ | n.t. | $10^6$ |

The $LD_{50}$ rates for chicks and mice according to table 1 show the lesser sensitivity of chicks towards S. tm, which has to be compensated by a lesser attenuation level of the vaccine strains.

b. Recognition of the *Salmonella typhimruium* vaccine strain optimally suited to chicks/chickens (with or without an rtt marker as an envelope mutation optimizing the vaccine strain) over the equivalent protective effect against a toxic infection conveyed by means of an i.p. or oral immunization.

The equivalent protective effects against an $LD_{75}$: toxic infection, effected two weeks later, which can be attained through a single i.p. immunization with the vaccine strain S. tm Nal 2/Rif 9 and the strains S. tm Pur-(i.p. $LD_{50}$ mouse $10^{7.5}$ cfu) and Zoosaloral (i.p. $LD_{50}$ $10^{8.2}$ cfu) being overattenuated for chicks, on the second day after hatching: see table 2;

oral immunization with S. tm Nal 2/Rif9, S. tm Nal 2/Rif 9/Rtt; as well as the calf vaccine Zoosaloral being overattenuated for chicks, within $\leq 36$ hours or on the fourth day after hatching: see table 3;

served as the criterion "optimal attenuation".**

TABLE 2

Attainable immunity against a toxic infection in the case of a single i.p. immunization with $10^6$ cfu of mutants having different attenuation levels on the second day of life; challenge with $3 \times 10^8$ cfu of the wild strain on the 16th day of life (mean of 3 exp.)

| i.p. immunization: $10^6$ cfu S. tm vaccine strain/test strain | i.p. challenge mortality (%) |
|---|---|
| Nal 2/Rif 9 | 25 |
| Pur~81 | 25 |
| Zoosaloral | 30 |
| control | 75 |

TABLE 3

Attainable immunity against a toxic infection in the case of a single oral immunization with $10^9$ cfu of the vaccine strains and Zoosaloral, being overattenuated for chicks; challenge with i.p. $3 \times 10^8$ cfu of the S. tm wild strain on the 16th day of life (mean of 4 experiments)

| S. tm vaccine strain/test strain | with (cfu) | oral immunization on 2-day mortality (%) | 4-day mortality (%) |
|---|---|---|---|
| Nal 2/ Rif 9 | $10^9$ | 23 | 35 |
|  | $10^8$ | 27 | n.t. |
| Nal 2/Rif 9/ Rtt | $10^9$ | 24 | 40 |
|  | $10^8$ | 26 | n.t. |
| Zoosaloral | $10^9$ | 42 | 60 |
|  | $10^8$ | 47 | 65 |
| control |  | 75 |  |

As shown in table 2, the single i.p. immunization with all vaccine strains reduces the mortality of an unphysiological toxic infection from about 75% to $\leq 30\%$.

As shown in table 3, this reduction in mortality as opposed to Zoosaloral and metabolism drift mutants having generation times of $\geq 33$ minutes and an i.p. $LD_{50} \geq 10^{6.5}$ cfu—can also be obtained by a single oral immunization with the vaccine strain S. tm 2/Rif 9 (with or without rtt marker), i.e., therefore, this vaccine strain is optimally attenuated for chicks.

Furthermore, table 3 shows the:

overattenuation of the calf vaccine Zoosaloral less protectively effective immunization against a toxic infection on the fourth day of life. Presumably, this is for reasons of the higher colonization resistance on the fourth day of life, which should influence the translocation and penetration rates of the vaccine strains.

EXAMPLE 5

S. tm, S. ent, S. inf and S. ana: Isolation of spontaneous antibiotic resistance clones as (single and) double marker vaccine strains being optimally attenuated for chicks/chickens by means of the "attenuation equivalent (prolonged) generation time" (see also example 1).

$10^9$ to $10^{10}$ cfu of the wild strain are transferred onto nutrient agar containing 400 ug streptomycin/ml by means of a spatula and incubated for approximately two days at 37° C. The resistance clones are transferred onto nutrient agar, controlled with respect to obtained resistance, in the preliminary test the less or more reduced extinction in comparison with the wild strain is determined (Spekol with tube samples, Zeiss-Jena, wave length 650 nm, starting germ count $10^7$ cfu, incubation in shaking water bath for 3 hours at 37° C.) (see example 1), and the generation times of clones appearing to be suitable are measured by means of the Abbott MS-2 test system. As described above, in the second step, from clones having generation times being prolonged by about 3 to 6 minutes rifampicin resistance clones (nutrient agar containing 400 ug rifampicin/ml) are obtained, the generation times thereof are determined, and Sm/Rif clones having generation times of about 28 to 32 minutes are favored as double marker vaccine strains. (The use of the Sm-stwd attenuation instead of the Nal-stwd attenuation is preferable, since the ssq marker (see example 6) as an envelope mutation—e. g. in Sm/Rif vaccine strains (upon abstaining from an Nal-stwd attenuation as a gyrase mutation)—also provides a hypersensitivity against the at present most effective antibiotic ciprofloxacin.)

EXAMPLE 6

Additional incorporation of an ssq ("safety and therapy") marker, optimizing the vaccine strain and increasing its acceptance, into the wild and vaccine strains, respectively. A fresh culture is suspended in PBS and treated with 100 ug/ml N-methyl-N-nitro-N-nitrosoguanidine (MNG, ZIMET, Jena) up to a survival rate of 10%. Then, it is incubated for 2 hours at 37° C. in nutrient bouillon containing 0.4 ug chloramphenicol, and treated in the conventional manner with 1000 IU penicillin/ml. Clones lacking growth are obtained by means of the stamping technique on nutrient agar containing 0.4 ug chloramphenicol (0.01 ug ciprofloxacin, 1.0 ug doxycycline)/ml. As ssq (supersensitivity to quinolons) strains such clones are determined and used as safety and therapy markers optimizing the vaccine strain and increasing its acceptance, which:

do not grow on nutrient agar containing 0.4 ug chloramphenicol, 0.01 ug ciprofloxacin or 1.0 ug doxycycline (as well as, mostly, 30 ug erythromycin)/ml, show a desirable reversion frequency of $\leq 10^7$.

The reversion frequency of the envelope mutation is better determined on nutrient agar containing 20 or 30 ug erythromycin/ml, since, upon the high germ counts, the rest growth shifts towards a two steps higher concentration of ciprofloxacin, chloramphenicol and doxycycline.

Suitable as vaccine strains are clones having an ssq marker, which, through mutagen treatment, undergo no or only a minor generation time prolongation/attenuation caused by co-mutation.

EXAMPLE 7

Recognition of the *S. typhimurium, S. enteritidis, S. infantis* and *S. anatum* vaccine strain being optimally attenuated for chicks/chickens by means of the detection of the obtained or residual invasive capacity of the metabolism drift (stwd) single marker mutants and double marker vaccine strains for chicks.

Chicks at the age of ≦36 hours were infected orally with $10^9$ cfu of the respective wild strains, stwd single marker mutants and stwd-double marker mutants, respectively. After five to eight days the chicks were killed, the liver extracted aseptically, was homogenized, transferred onto nutrient agar, and the remaining material was mixed with nutrient bouillon. The grown colonies and cultures, respectively, were controlled with respect to O-group identity and marker.

With respect to *S. typhimurium* and *S. enteritidis,* after five days the germ counts/gram liver are in the range of about $10^3$ cfu, after eight days they are in the range of about $10^2$ cfu. In contrast to that, with respect to *S. infantis* and *S. anatum,* the germ counts are in the border area of quantitative determination at about $10^1$ to ≦$10^2$ cfu, and after eight days the detection often can only be obtained by means of propagation. These lower germ counts/gram liver, found with respect to *S. infantis* and *S. anatum,* apparently correlate with U. Methner's observation (doctoral thesis, University of Leipzig, Veterinary Medical Faculty, 1991) that *S. infantis* is less invasive for chicks.

The generally obtained invasive capacity of the favored vaccine strains (and single marker mutants) which determined from the numbers of colonies incubated does not quite reach the figures of the homologous wild strains, apparently is essential for the vaccination success (Barrow, P. A. et al., *Res. Microbiol.,* 1990, 141, pp. 851–853).

EXAMPLE 8

Determination of the frequency in percentages-and the duration of excretion of the S. tm Nal 2/Rif 9 vaccine strain (with or without rtt marker) after oral immunization of ≦36 hours old chicks, and of the S. tm Nal 2/Rif-9 after oral immunization of five days old chicks.

The frequency in percentages in the tested stool samples and the maximum detectable duration of excretion of the vaccine strain with or without rtt marker, dependent upon the chicks' age upon oral immunization is shown in FIG. 1.

FIG. 1 shows the frequency (percentage of positive samples after propagation) and duration (last positive result, border of detection about 10 germs/gram stool) of excretion of the vaccine strains S. tm Nal 2/Rif 9 without (●—) and with ftt marker (▲—) after a single oral immunization of ≦36 hours old chicks with $10^9$ cfu as well as with S. tm Nal 2/Rif 9 (individual figures not shown, (—)) on the fourth day of life. (Mean of four to five experiments)

The following facts are shown in FIG. 1:

upon immunization within ≦36 hours after hatching, the S. tm Nal 2/Rif 9 is excreted over the 32 days tested. After incorporating the rtt marker, the vaccine strain can rarely be detected three weeks after the immunization.

upon immunization on the fourth day, the S. tm Nal 2/Rif 9 (without rtt marker) can only be detected occasionally after the 18th day, apparently caused by the already existing colonization resistance caused by anaerobic bacteria.

the frequency in percentages of positive accumulation cultures is analogous to this.

With respect to the oral immunization within ≦36 hours, the S. tm Nal 2/Rif 9 can still be detected in about 90% of the samples, with respect to the vaccine strain having been optimized with the rtt marker, only about 40% of the stool samples are still positive.

The colonization dynamism of the favored vaccine strains S. tm Ssq/Sm 60/Rif 42, S. ent Ssq/Sm 24/Rif 12 g, S. inf Ssq/Sm 153/Rif 7 and S. ana Ssq/Sm 81 /Rif 21 was determined in that, after oral application of $10^9$ cfu within ≦36 hours after hatching, the portion of the respective salmonella vaccine strain in the enterobacteria flora of the stool samples over a duration of two weeks was tested, wherein the favored vaccine strains (see. above) showed an excretion behavior comparable to the vaccine strain S. tm Nal 2/Rif 9/Rtt.

EXAMPLE 9

Reduction of the quantitative excretion of homologous neutrally Nal/Sm marked wild strains in immunized chicks in comparison with controls.

The ≦36 hours old chicks which received a monovalent oral immunization by the vaccine strains S. tm Nal 2/Rif 9/Rtt, S. tm Ssq/Sm 60/Rif 42, S. ent Ssq/Sm 24/Rif 12, S. ent Ssq/Sm 24/Rif12k, S. ent Ssq/Sm 24/Rif 12g, S. ent Ssq/Sm 24/Rif 3, S. inf Ssq/Sm 153/Rif 7 and S. ana Ssq/Sm 81/Rif 21, respectively were infected with $10^6$ (partly $10^7$) cfu of the respective homologous wild strain on the 17th day of life, parallel to controls of the same age.

In comparison with the controls, the immunized chicks in compliance with the results obtained with respect the S. tm prototype vaccine strain Nal 2/Rif 9—show a significantly reduced excretion of the wild strain, especially in the first five to ten days after the oral challenge (determined from the enterobacteria colonization density in thousandth). The variation (reducing with time) lies in the range of up to two tenth powers. From the sixth to the tenth day after the oral challenge, the salmonella colonization densities in immunized chicks come into closer alignment with those of the controls (in the 0.1 thousandth range of enterobacteria germ counts). In individual cases, however, immunized chicks may show a reduced excretion in the range of one log step, even after the tenth day.

A complete elimination of the salmonella bacteria within the individual infected animal can hardly be expected, since, apart from *S. gallinarum pullorum,* these pathogens apparently behave like a "normal flora" within chicks. The highly reduced excretion with respect to immunized chicks/chickens should, in the medium term, lead to a salmonella free chicken stock, in combination with hygiene measures.

EXAMPLE 10

Increased sensitivity towards detergents

The vaccine strains S. tm Ssq/Sm 60/Rif 42, S. ent Ssq/Sm 24/Rif 12, S. ent Ssq/Sm 24/Rif 12k, S. ent Ssq/Sm 24/ Rif 12g, S. ent Ssq/Sm 24/Rif 3, S. inf Ssq/Sm 153/Rif 7, S. ana Ssq/Sm 81/Rif 21, S. tm Nal 2/Rif 9/Rtt show in comparison to wild strains an increased sensitivity towards anionic detergents, especially towards sodium dodecyl sulphate (SDS). So the vaccine strains do not show growth on appropriate nutrient media (approximately without proteins) at a concentration of 0.5 mg SDS/ml the wild strains grow at 5 mg SDS/ml.

Vaccine strains suspended in physiological solution of sodium chloride become lysed at room temperature within 30 minutes to about 90% whereas wild strains show only a lysis rate of about 10%.

It can be concluded from these observations that the vaccine strains have an increased sensitivity resp. reduced capability of survival in the environment especially if measures for hygienic cleaning are taken.

EXAMPLE 11

The separation of vaccine strains from wild strains with respect to:

S. tm Ssq/Sm 60/Rif 42, S. ent Ssq/Sm 24/Rif 12, S. ent Ssq/Sm 24/Rif 12k, S. ent Ssq/Sm 24/Rif 12g, S. ent Ssq/Sm 24/Rif 3, S. inf Ssq/Sm 153/Rif 7 and S. ana Ssq/Sm 81/Rif 21 is obtained by their resistance against 100 ug rifampicin and 200 ug streptomycin/ml nutrient agar as well as the missing growth on nutrient agar containing 0.4 ug chloramphenicol (or 0.01 ug ciprofloxacin, 1.0 ug doxycycline and 30 ug erythromycin, respectively)/ml.

S. tm Nal 2/Rif 9/Rtt is obtained by its resistance against 100 ug rifampicin and 12.5 ug nalidixic acid*/ml nutrient agar as well as the missing growth on nutrient agar containing 30 ug erythromycin/ml.

*(The reduced resistance of the rtt strain against nalidixic acid in comparison with the initial Nal 2/Rif 9 strain is a consequence of the rtt mutation (incorporated later) leading to a varied permeability of the outer membrane.)

EXAMPLE 12

Mass culture, preparation and use of vaccine strains.

For the production of live vaccines (double marker vaccine strains without ssq marker or) triple marker vaccine strains with ssq marker are incubated in a suitable full medium as a liquid culture until the end of the logarithmic phase. The bacterial suspensions are mixed with a conventional stabilizer and lyophilized.

The vaccine strains obtained in this manner are usually applied to ≦36 hours old chicks in a single dose of $10^8$ to $10^9$ cfu. Chickens usually receive a single immunization/boostering of $10^9$ cfu orally, or about $10^8$ cfu parenterally, prior to the laying period.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. Although the invention has primarily been described with reference to Salmonella vaccines, the inventive methods should be applicable to producing vaccines and methods of protecting against acquiring disease from handling vaccine or ingesting vaccinated poultry when the vaccine is directed to Shigella, Listeria, Pasteurella, Campylobacter and *E. coli,* as well.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of reducing intestinal colonization by a wild strain of *Salmonella typhimruium* in ≦36 hour-old chicks by oral administration with a therapeutically effective amount of a live attenuated mutant of *S.typhimurium*, Nal2/Rif9/Rtt.

* * * * *